(12) United States Patent
Tullberg et al.

(10) Patent No.: US 9,584,135 B2
(45) Date of Patent: *Feb. 28, 2017

(54) INTERFACE AND RELATED METHOD FOR CONNECTING SENSOR EQUIPMENT AND A PHYSIOLOGICAL MONITOR

(71) Applicant: ST. JUDE MEDICAL COORDINATION CENTER BVBA, Zaventem (BE)

(72) Inventors: Mattias Tullberg, Uppsala (SE); Mattias Dahlberg, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/088,631

(22) Filed: Apr. 1, 2016

(65) Prior Publication Data

US 2016/0218720 A1 Jul. 28, 2016

Related U.S. Application Data

(62) Division of application No. 13/801,870, filed on Mar. 13, 2013, now Pat. No. 9,325,326.

(51) Int. Cl.
*H03L 5/00* (2006.01)
*A61B 5/00* (2006.01)
*A61B 5/021* (2006.01)

(52) U.S. Cl.
CPC ............... *H03L 5/00* (2013.01); *A61B 5/021* (2013.01); *A61B 5/7203* (2013.01);
(Continued)

(58) Field of Classification Search
CPC ............................... H03L 5/00; A61B 5/7225
(Continued)

(56) References Cited

U.S. PATENT DOCUMENTS 5,568,815 A 10/1996 Raynes et al.
8,187,195 B2 * 5/2012 Tulkki ................ A61B 5/0215
600/486
(Continued)

FOREIGN PATENT DOCUMENTS

EP 0 712 603 A2 5/1996
JP 08-299286 A 11/1996

OTHER PUBLICATIONS

"Blood pressure transducers", American National Standard, ANSI/AAMI BP22: 1994/(R) (2006), 5 pgs.
(Continued)

*Primary Examiner* — Ryan Jager
(74) *Attorney, Agent, or Firm* — Foley & Lardner LLP

(57) ABSTRACT

An interface to connect sensor equipment and a physiological monitor includes a first connector to receive power from a first channel of the monitor and a second connector to receive power from a second channel of the monitor. The power from each of the first and second channels of the monitor is combined within the interface. The interface further includes a third connector to provide the combined power to the sensor equipment; a voltage converter to rescale the voltage of the combined power that is provided to the sensor equipment; and a scaling circuit to reduce the voltage of a signal representing a measured physiological parameter. The signal representing the measured physiological parameter is sent from the sensor equipment to the monitor. The interface is advantageous to allow sensor equipment to be sufficiently powered by a monitor that would not typically provide enough power.

14 Claims, 5 Drawing Sheets

(52) U.S. Cl.
CPC .... *A61B 5/7225* (2013.01); *A61B 2560/0204* (2013.01); *A61B 2562/22* (2013.01); *A61B 2562/222* (2013.01); *A61B 2562/225* (2013.01)

(58) Field of Classification Search
USPC ........................................ 600/300, 385, 509
See application file for complete search history.

(56) References Cited

U.S. PATENT DOCUMENTS

| | | | |
|---|---|---|---|
| 2006/0073728 A1 | 4/2006 | Zaiken et al. | |
| 2010/0198085 A1* | 8/2010 | Knoll ................... | A61B 5/0215 600/485 |
| 2012/0178287 A1* | 7/2012 | Mantay ................. | H01R 31/06 439/505 |
| 2014/0058213 A1* | 2/2014 | Abu-Tarif ............ | A61B 5/0205 600/301 |

OTHER PUBLICATIONS

"CARESCAPE Monitor B650", GE Healthcare, (2010), 4 pgs.
"Functional Management: SmartMap® Pressure Instrument", Volcano Corporation, http://www.volcanocorp.com/products/smartmap-pressure-instrument.php , (2013), 2 pgs.
"PressureWire™ Aeris™ How to Set-up PressureWire Aeris and Perform an FFR Procedure", St. Jude Medical, (2011), 13 pgs.
"PressureWire™ Aeris™ with Agile Tip Technology", St. Jude Medical, http://www.sjmprofessional.com/Products/Intl/Intravascular-Sensors/PressureWire-Aeris , (2012), 6 pgs.
"RadiAnalyzer™ Xpress Set-up", St. Jude Medical, (2010), 14 pgs.
International Search Report dated Sep. 3, 2014, 12 pgs.
Japanese Office Action and English translation, Jul. 26, 2016, 14 pages.
Canadian Office Action dated Sep. 8, 2016, 4 pages.

* cited by examiner

INTERFACE AND RELATED METHOD FOR CONNECTING SENSOR EQUIPMENT AND A PHYSIOLOGICAL MONITOR

CROSS-REFERENCE TO RELATED APPLICATIONS

This application is a divisional application of U.S. application Ser. No. 13/801,870, filed Mar. 13, 2013, the entire contents of all of which are incorporated herein by reference.

BACKGROUND

The present invention relates generally to an interface for connecting sensor equipment to a monitoring system.

Various physiological parameters of a patient are monitored during many medical procedures. These physiological parameters may be blood pressure, temperature, rate-of-fluid flow, or other vital signs that provide the physician or medical technician with critical information related to the status of a patient's condition.

One device that is widely used to monitor physiological parameters is the blood pressure sensor. A blood pressure sensor is often included in a sensor guide wire for intravascular measurements. The blood pressure sensor senses a patient's blood pressure and provides a representative electrical signal that is transmitted to the exterior of the patient. For most applications, the sensor must be electrically energized. To transmit energy and the signal representative of the patient's blood pressure, thin electrical leads are often provided inside the guide wire. The guide wire is generally in the form of a tube (e.g., having an outer diameter of 0.35 mm), which is often made of stainless steel.

Monitoring systems are used in a medical environment to receive and process information related to the patient's physiological parameters. A sensor (e.g., a blood pressure sensor) may be directly connected to a monitor of the monitoring system via a sensor guide wire. Alternatively, the sensor may be connected to the monitor via a receiver or other intermediary device. In one embodiment utilizing a receiver, the sensor guide wire sends a wireless signal to the receiver, which is directly connected to the monitor. The monitor typically includes a channel used to connect the sensor equipment (e.g., the sensor guide wire or the receiver) to the monitor. Through this channel, the sensor equipment may be powered by the monitor.

SUMMARY

The BP22 standard (ANSI/AAMI BP22: 1994/(R)2006) (referred to herein as "BP22") governs performance and safety requirements for transducers, including cables, designed for blood pressure measurements. In particular, the connection between sensor equipment and physiology monitors is governed by the BP22 standard. Many currently existing monitors include channels that comply with the BP22 standard. Such monitors can provide power larger than or equal to 80 mW. However, certain monitors do not have channels that comply with the BP22 standard, and these monitors may not be able to provide sufficient power to sensor equipment connected to the monitor. In other circumstances, even if the monitors generally comply with the BP22 standard, the sensor equipment may require more power than the monitor can provide.

According to one exemplary embodiment of the present invention, an interface to connect sensor equipment and a monitor includes a first connector to receive power from a first channel of the monitor and a second connector to receive power from a second channel of the monitor. The power from each of the first and second channels of the monitor is combined within the interface. The interface further includes a third connector to provide the combined power to the sensor equipment; a voltage converter to rescale the voltage of the combined power that is provided to the sensor equipment; and a scaling circuit to reduce the voltage of a signal representing a measured physiological parameter. The signal representing the measured physiological parameter is sent from the sensor equipment to the monitor.

According to another exemplary embodiment, a method for connecting sensor equipment and a monitor includes combining a power signal from a first channel of the monitor and a power signal from a second channel of the monitor to form a combined power signal; rescaling the voltage of the combined power signal; providing the combined power signal to the sensor equipment; and adapting the voltage of a signal representing a measured physiological parameter, which is sent from the sensor equipment to the monitor.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate exemplary embodiments in detail, it should be understood that the invention is not limited to the details or methodology set forth in the description or illustrated in the figures.

Figure 1:
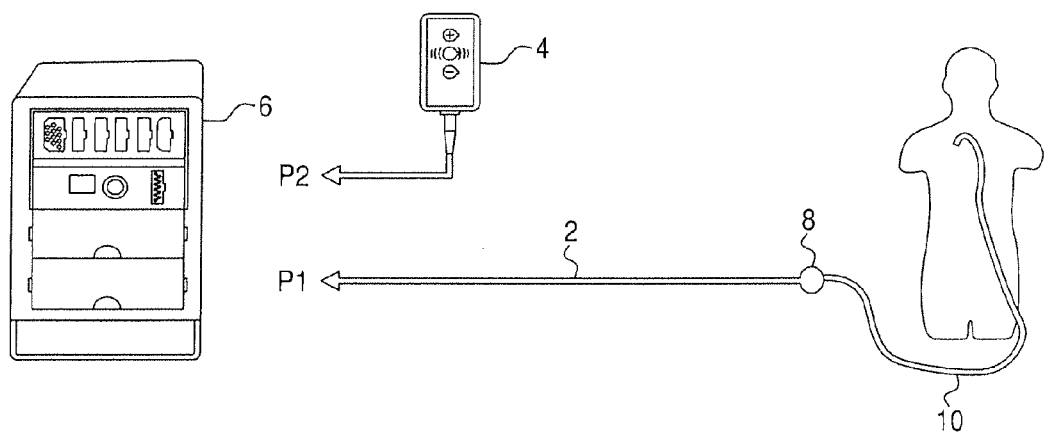
FIG. 1 is a schematic diagram of a medical system for measuring physiological parameters, according to an exemplary embodiment.

Referring to FIG. 1, a system for measuring physiological parameters according to an exemplary embodiment includes a sensor wire 2, a receiver 4, and a monitor 6. "Sensor equipment" may include either or both of the sensor wire 2 and the receiver 4, as well as any other type of sensor equipment that a user may desire to connect to a monitor for receiving and processing information related to physiological parameters. For example, sensor equipment can include equipment used to measure any number of physiological parameters, such as ECG, $SpO_2$, non-invasive blood pressure, invasive blood pressure, temperature, or cardiac output. The sensor wire 2 or the receiver 4 may be connected to the monitor 6 to receive power from the monitor 6 using various circuits described herein.

The monitor 6 is part of a monitoring system for receiving, processing, and outputting information related to the patient's measured physiological parameters. The monitor 6 can be any monitor that has channels for direct connection of sensor equipment (e.g., a sensor wire 2 or a receiver 4). In FIG. 1, the monitor 6 includes pressure channels for sensor equipment used to measure a patient's aortic blood pressure (P1) and distal blood pressure (P2). In one embodiment, the monitor 6 is the GE CARESCAPE MONITOR B650, produced by GE HEALTHCARE. The GE CARESCAPE MONITOR B650 is described in manuals that can be found on GE HEALTHCARE's website, for example at: http://www.gehealthcare.com/siteplanning/docs/B650%20cut%20sheet.pdf. Information accessible through the GE HEALTHCARE website and related to the GE CARESCAPE MONITOR B650 on the filing date of this patent specification is hereby incorporated by reference herein in its entirety.

In one embodiment, the sensor wire 2 is connected to a pressure transducer 8, which is used to measure the patient's aortic blood pressure. The sensor wire 2 conveys information related to the patient's aortic blood pressure, as measured by pressure transducer 8, to the monitor 6. A common procedure for measuring aortic pressure is to connect a pressure transducer 8 to a guide catheter 10 located in a patient's aorta. The sensor wire 2 is directly connected to the monitor 6.

Figure 5:
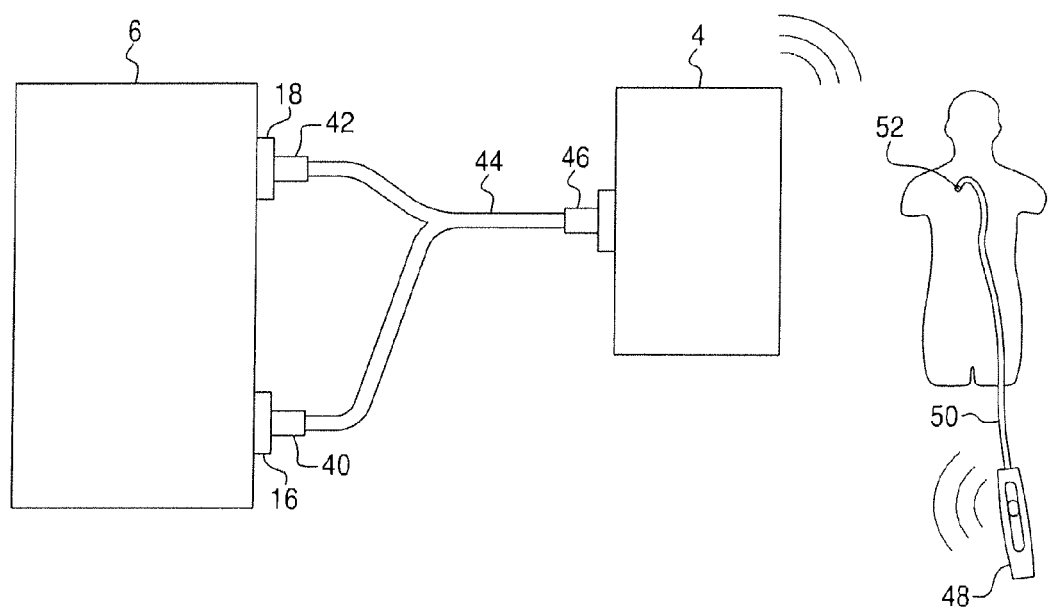
FIG. 5 is a schematic representation of a cable containing a circuit to connect sensor equipment to a monitor, according to an exemplary embodiment.

The receiver 4 conveys information related to the patient's distal blood pressure to the monitor 6. To measure distal blood pressure, the distal end of a sensor guide wire having a pressure transducer 52 (shown in FIG. 5) is inserted into the body of a patient, for example into an opening into the femoral artery, and placed at a desired location. In one embodiment, the pressure transducer 52 measures the blood pressure distal to a stenosis in the patient's coronary artery. Measurement of aortic and distal blood pressure (and subsequent calculation of fractional flow reserve) is a way to diagnose, for example, the significance of a stenosis. A transmitter 48 is electrically connected to a sensor guide wire 50 to wirelessly transmit blood pressure information to the receiver 4, which is correspondingly configured to receive wireless signals from the transmitter 48 (FIG. 5). The receiver 4 is connected to the monitor 6 to transmit the blood pressure information to the monitor 6. In one embodiment, the receiver 4 is the PRESSUREWIRE AERIS RECEIVER developed by ST. JUDE MEDICAL. One suitable sensor guide wire is described in U.S. Pat. No. 8,187,195, which is incorporated by reference herein in its entirety for the components, systems, and methods described therein related to physiological monitoring.

Figure 2:
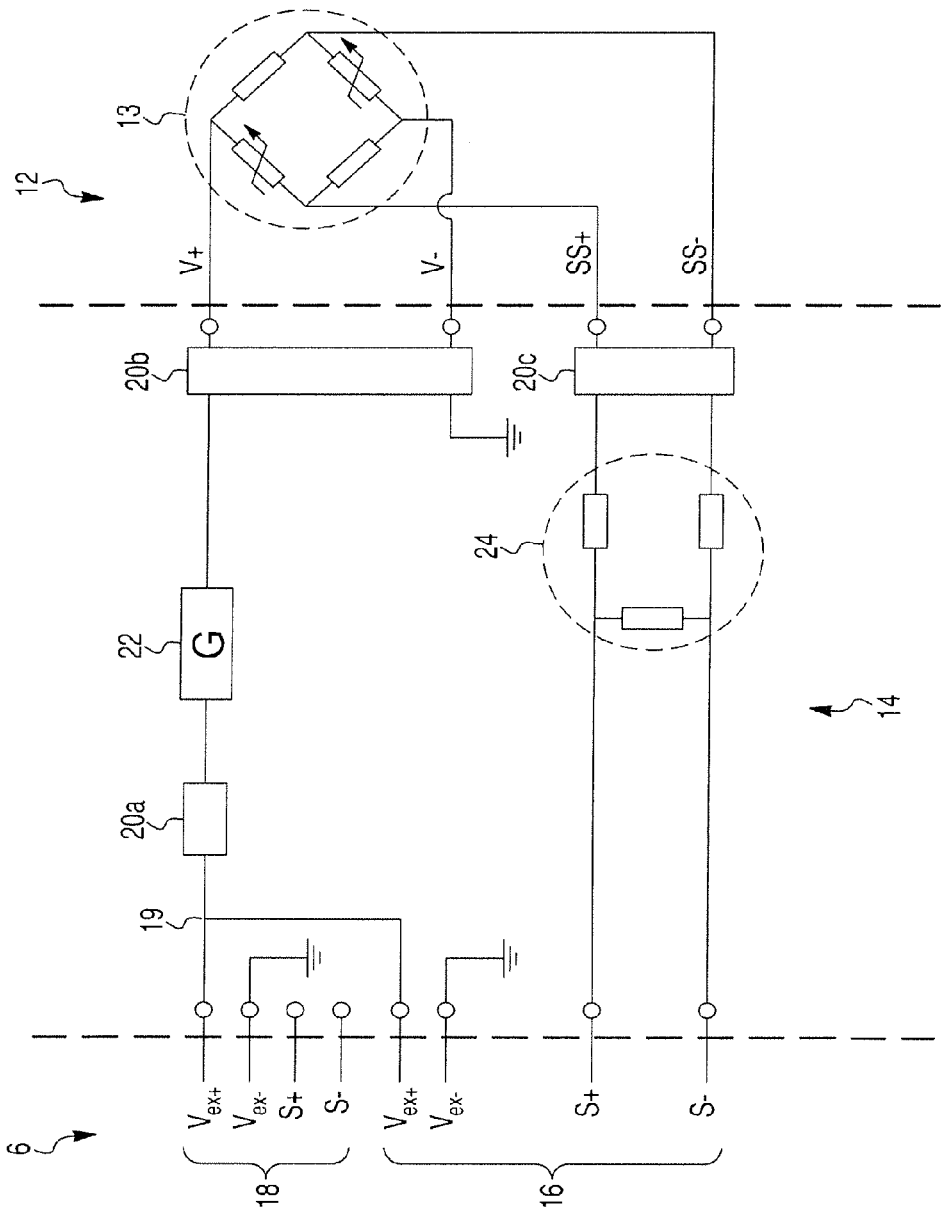
FIG. 2 is a circuit diagram representing a circuit to connect sensor equipment to a monitor, according to an exemplary embodiment.
Figure 3:
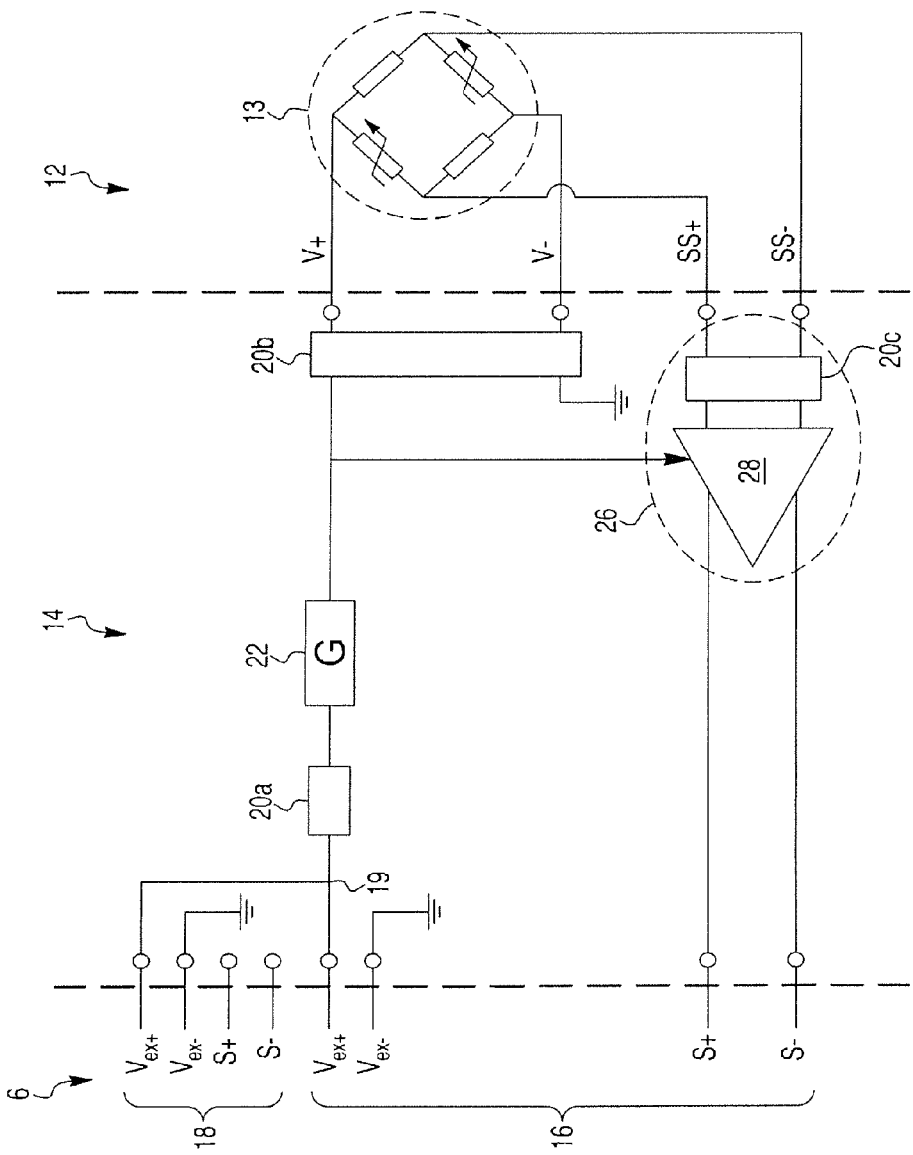
FIG. 3 is a circuit diagram representing a circuit to connect sensor equipment to a monitor, according to another exemplary embodiment.
Figure 4:
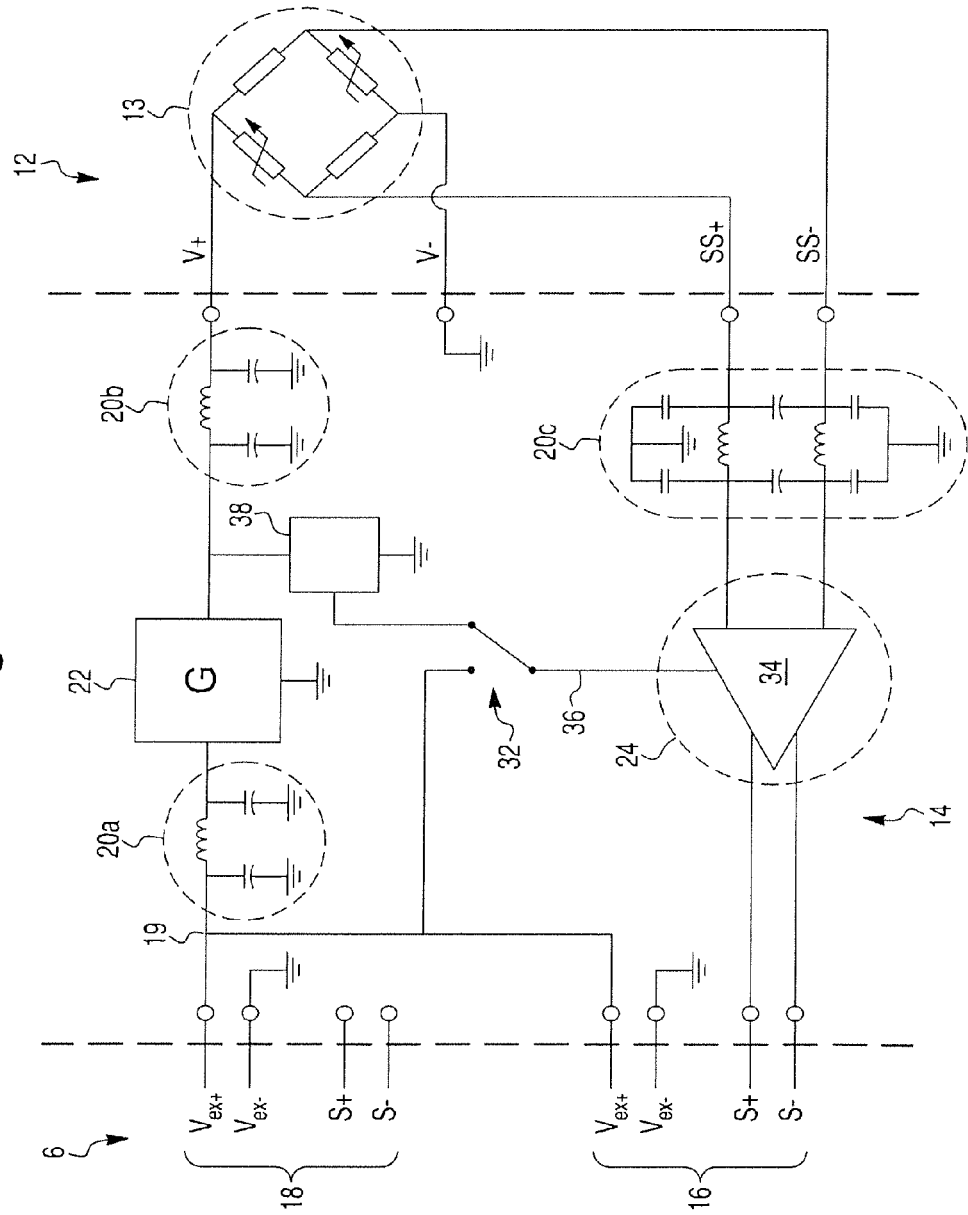
FIG. 4 is a circuit diagram representing a circuit to connect sensor equipment to a monitor, according to yet another exemplary embodiment.

Some types of sensor equipment receive power from the monitor to which they are connected. For example, in FIG. 1, the receiver 4 may receive power from the monitor 6. However, the channels of certain monitors are not configured to provide sufficient power to the sensor equipment, such as receiver 4, to allow the sensor equipment to operate as intended. These monitors may not provide sufficient power because they do not comply with the BP22 standard or because the sensor equipment requires more power than the monitor is able to provide. Accordingly, various embodiments of circuitry 14 described in connection with FIGS. 2-4 provide a connection between sensor equipment 12 and a monitor 6 to allow the sensor equipment to be adequately powered by the monitor 6. The circuitry 14 can be embodied in any suitable form of hardware, such as within a cable to connect the sensor equipment and the monitor. The cables described herein, which contain circuitry 14, therefore serve as an interface between sensor equipment 12 and monitor 6 that allow the sensor equipment 12 to receive sufficient power from monitor 6.

Referring to FIG. 2, a circuit diagram according to an exemplary embodiment illustrates the electrical connection between sensor equipment 12 and a monitor 6. The sensor equipment 12 may include a Wheatstone Bridge 13. Traditionally, a blood pressure transducer has consisted of a pressure responsive diaphragm that is mechanically coupled to piezoresistive elements connected in a Wheatstone Bridge-type circuit arrangement. When the diaphragm is placed in fluid communication with a body cavity (such as within the arterial or venous system), pressure induced deflections of the diaphragm cause the resistive elements to be stretched (or compressed, depending on their orientation). According to well-known principles, this alters the resistance of the elements in a manner that is related to the applied pressure. The magnitude of the applied pressure can thus be detected by applying an excitation power signal (usually in the form of a voltage) to the inputs of the Wheatstone bridge circuit, and by simultaneously monitoring the bridge output signal. The magnitude of that signal reflects the amount by which the bridge resistance has changed, according to Ohm's law.

Typically, an electrical cable connects the Wheatstone bridge portion of the transducer sensor to a transducer amplifier circuit contained within the vital signs monitor, such as the monitor 6 shown in FIG. 1. Channels of the monitor 6 (e.g., for the connection of sensor equipment via a cable) are illustrated in FIG. 2 as first channel 16 and second channel 18. The amplifier circuit within monitor 6 supplies the excitation power signal to the Wheatstone bridge, and simultaneously monitors the bridge output signal. The excitation power signal is typically in the form of a voltage and, depending on the monitor type and manufacturer, can have varying magnitudes and formats, both time-varying (sinusoidal, square-waved and pulsed) and time independent (DC). According to the principles under which conventional Wheatstone-bridge transducers operate, transducer amplifier circuits in most patient monitors have been designed to expect a sensor output signal having a magnitude that is proportional to the magnitude of the excitation power signal and also proportional to the magnitude of the sensed pressure.

Referring again to FIG. 2, circuitry 14 connects the sensor equipment 12 to a monitor (such as the monitor 6 shown in FIG. 1). The circuitry 14 can be included within a cable that can be connected to multiple ports of a monitor 6. In conventional connections between sensor equipment and a monitor, a cable connects the sensor equipment to a single channel of the monitor. However, the cable 44 or other physical interface that includes circuitry 14 connects to two channels of the monitor 6 (see FIG. 5). Accordingly, the cable 44 or other physical interface has a first connector 40 and a second connector 42, shown schematically in FIG. 5. Although shown in separate housings, the first connector 40 and second connector 42 can be contained within a single housing that provides two connections to the monitor 6. The first connector 40 can be operatively coupled to the first channel 16 of monitor 6 to receive an excitation power signal from monitor 6. Similarly, the second connector 42 can be operatively coupled to the second channel 18 to receive another excitation power signal from monitor 6. At least one of the channels (e.g., first channel 16) receives a signal representing a measured physiological parameter from the sensor equipment via one of the connectors (e.g., first connector 40). For example, in FIG. 2, a connector operatively couples to the first channel 16 in order to allow transmission of: 1) an excitation signal from the monitor 6 to the sensor equipment 12, and 2) a signal representing the measured physiological parameter from the sensor equipment 12 to the monitor 6. The cable 44 (FIG. 5), which includes circuitry 14, therefore provides an interface that allows the sensor equipment 12 to obtain power from two channels of a monitor 6, rather than one. This feature allows sensor equipment 12 to be used with monitors 6 that do not provide sufficient power through a single channel to operate the sensor equipment 12 (e.g., for use with monitors that do not comply with the BP22 standard or with sensor equipment that requires more power than a monitor can provide).

As noted above, monitor 6 includes a first channel 16 and a second channel 18. In the embodiment of FIG. 2, the first channel 16 both receives a signal from the sensor equipment 12 and provides an excitation power signal in the form of a voltage. The voltages provided by the channels 16, 18 are represented as $V_{ex}$ in FIGS. 2-4. The signal lines transmitting the pressure or other signals representing physiological parameter(s) to the monitor 6 are represented in FIGS. 2-4 as "S." The second channel 18 of the monitor 6 provides an additional excitation power signal to the sensor equipment 12. The excitation power signals from the first channel 16 and the second channel 18 of the monitor 6 are combined within circuitry 14 prior to being supplied to the sensor equipment 12. By combining the power from two channels of the monitor 6, a cable that includes circuitry 14 allows sensor equipment 12 to be used with monitors that would not provide sufficient power through a single channel. In one embodiment, the power supplied by each channel 16, 18 is 50 mW. If the sensor equipment 12 requires 80 mW, sufficient power can be obtained by using both channels 16, 18 (which would provide a total of 100 mW).

Circuitry 14 further includes one or more filters 20a, 20b to limit noise. The filters can be passive filters, active filters, or any other type of suitable filter. A DC to DC converter 22 rescales the voltage supplied by the monitor 6 to the sensor equipment 12. In one embodiment, the voltage is rescaled because the sensor equipment 12 requires a higher voltage to operate than is provided by the monitor 6. In one example, each channel 16, 18 provides 2.5V, and the sensor equipment 12 requires 4-8V and 20 mA to operate. The DC to DC converter 22 therefore increases the voltage from 2.5V to a voltage between 4-8V. In one embodiment, the converter 22 is a voltage doubler that increases the voltage from 2.5V on the input side to 5.00V on the output side.

Once the sensor equipment 12 has been used to measure one or more physiological parameters, such as blood pressure, the signal representing the measured physiological parameter is transmitted through a scaling circuit 24. Scaling circuit 24 adapts the voltage. In one embodiment, scaling circuit 24 reduces the voltage, and in yet another embodiment the scaling circuit 24 is a voltage divider. The scaling circuit 24 can include resistors or any other combination of components that adapts the voltage difference between the S+ and S− signal lines. The voltage is adapted by scaling circuit 24 because the monitor 6 is configured to receive a certain voltage (e.g., 2.5V) from the sensor equipment 12. For example, the monitor 6 may be configured to receive 12.5 mV for each millimeter of Hg of pressure. In the example described above in which each channel provides 2.5V and the sensor equipment requires 4-8V to operate, the converter 22 doubles the voltage provided to sensor equipment 12. Scaling circuit 24 therefore halves the voltage in order for the monitor 6 to accurately convert the received signal to a physiological parameter measurement (e.g., to a blood pressure measurement). In one embodiment, the monitor 6 assumes that the impedance of the sensor equipment 12 is high enough not to load the excitation voltage (e.g., 2.5V). Thus, the monitor 6 expects to receive a signal having a voltage directly related to the excitation voltage (e.g., 2.5V) from the sensor equipment 12. If the sensor equipment 12 is configured to return a signal representing blood pressure, the monitor 6 monitors the difference between the S+ and the S− signal lines and converts the difference to a corresponding pressure reading. By rescaling the voltage provided to the sensor equipment 12 and then adapting the return signal, the circuitry 14 provides an interface that allows the sensor equipment 12 (e.g., a receiver 4) to be supplied with a sufficient voltage while ensuring that the monitor 6 can accurately convert the return signal to a physiological parameter measurement (e.g., a blood pressure measurement).

Referring to FIG. 3, a circuit diagram illustrates an additional exemplary embodiment of an electrical connection between sensor equipment 12 and a monitor 6. Similar to the embodiment of FIG. 2, circuitry 14 serves as an interface between sensor equipment 12 (including a Wheatstone Bridge 13) and a monitor 6. Circuitry 14 combines the power excitation signals from a first channel 16 and a second channel 18 to provide sufficient power to the sensor equipment 12, allowing the sensor equipment 12 to be used with monitors that may not provide sufficient power through a single channel.

The circuitry 14 of FIG. 3 includes a scaling circuit 26 to modify the signal from the sensor equipment 12 to the monitor 6. The scaling circuit 26 scales the signal from the sensor equipment 12 to a constant sensitivity. In one embodiment, the scaling circuit 26 includes a voltage-controlled amplifier 28 and a capacitor 30; however, other circuits that use a reference voltage to scale, such as an ADC-microcontroller-DAC construct, may be used. The scaling circuit 26 also includes components to accomplish the same functions as scaling circuit 24, described in connection with FIG. 2. In other words, scaling circuit 26 scales the signal to a voltage interpretable by the particular monitor 6. The function of scaling the signal provided to the monitor 6 can be accomplished by using one or more scaling circuits containing a variety of different components.

The inclusion of scaling circuit 26 in FIG. 3 changes the requirements related to the DC to DC converter 22 relative to the embodiment of FIG. 2. In the embodiment of FIG. 2, the converter 22 must provide a voltage stable enough to be used by the sensor equipment 12, scaled by the scaling circuit 24, and interpreted by the monitor in a manner that yields an accurate pressure reading (or reading of another physiological parameter). In other words, the FIG. 2 design (in order to be accurate) requires that the voltage doubler accurately double the voltage (e.g., within 0.5%). However, in FIG. 3, the presence of a scaling circuit 26 allows for the use of a less accurate (or less stable) converter 22 because the scaling circuit 26 will adapt the signal from the sensor equipment 12 dependent on the actual voltage provided to the Wheatstone Bridge 13. The signal is scaled by the scaling circuit 26 such that the signal sent to the monitor 6 will be accurately interpreted by the particular monitor 6. The inclusion of a scaling circuit 26 that scales based on the actual voltage applied to the Wheatstone Bridge 13 therefore allows the use of a less precise (cheaper) converter 22.

FIG. 4 illustrates a still further exemplary embodiment of the electrical connection between sensor equipment 12 and a monitor 6. In this embodiment, circuitry 14 allows a user to choose (e.g., via a switch 32) whether the signal received by the monitor 6 is scaled based on a fixed reference level or based on the excitation voltage from first and second channels 16, 18. As in previous embodiments, the excitation power signals provided by the first channel 16 and the second channel 18 are combined in the embodiment of FIG. 4. Filters 20a, 20b filter noise. Although specific filter embodiments are shown in FIG. 4, the filters 20a and 20b can be passive filters, active filters, or any other type of suitable filter. In one embodiment, one or both of filters 20a and 20b are low pass filters. The embodiment of FIG. 4 includes a DC to DC converter 22 to rescale the input voltage. In one embodiment, the converter 22 increases the voltage, and in yet another embodiment the converter 22 doubles the voltage. After measurement of the relevant physiological parameter (e.g., blood pressure), the sensor equipment 12 provides a signal representing the measured parameter to a third filter 20c. The filter 20c can be active, passive, or any other type of suitable filter. In one embodiment, the third filter 20c is a differential low pass filter, which reduces signal noise.

The scaling circuit 24 of FIG. 4 includes a buffer amplifier 34. The buffer amplifier 34 includes a reference input 36. The switch 32 allows a user (or manufacturer) to switch the reference input 36 from a fixed reference voltage provided by reference voltage source 38 and the excitation voltage provided by monitor 6 (e.g., at intersection 19). When the switch 32 is in the first position (the position shown in FIG. 4), the reference input 36 has a fixed voltage as a result of reference voltage source 38. However, when the switch 32 is switched to the second position, reference input 36 will have a voltage equal to the excitation voltage provided by monitor 6. Certain monitors are configured to use a fixed reference to interpret the signal received from sensor equipment 12. If circuitry 14 of FIG. 4 is being used to interface these monitors to sensor equipment 12, the switch should be in the position shown in FIG. 4 such that the signal received by the monitor 6 is scaled based on a fixed reference voltage. However, other monitors are configured to use the excitation voltage provided by the monitor as a reference by which to interpret the signal received from sensor equipment 12. To use the circuitry 14 of FIG. 4 with these systems, the switch 32 should be in the second position, which enables the signal received from the sensor equipment 12 to be scaled using the excitation signal provided by the monitor as the reference voltage.

FIG. 5 illustrates a schematic diagram of a cable 44 that includes circuitry 14 according to any of the embodiments described herein. As described above, the cable 44 includes a first connector 40 and a second connector 42 that can be operatively coupled to the first and second channels 16, 18, respectively, of a monitor 6. The connectors 40, 42 allow excitation power signals to be transmitted from the monitor 6 to the cable 44, through circuitry 14 contained within cable 44, and to the sensor equipment (such as receiver 4). The connectors 40, 42 further allow a signal representing a measured physiological variable to be transmitted from the sensor equipment, through circuitry 14, and to the monitor 6. In one embodiment, the signal representing a measured physiological variable is transmitted via connector 40 to the monitor 6. As shown in FIG. 5, the cable 44 further includes a third connector 46. The third connector 46 can be operatively coupled to the sensor equipment, such as a receiver 4, to transmit power from the monitor 6 to the sensor equipment. The receiver 4 may receive information representing measured blood pressure from a transmitter 48, which is connected to a sensor wire 50 having a pressure transducer 52. In one embodiment, the sensor wire 50 is a PRESSURE WIRE AERIS™ developed by ST. JUDE MEDICAL.

Several advantages arise from using the circuitry 14 described herein. In effect, circuitry 14 provides an interface that allows a monitor to provide sufficient power to sensor equipment. This feature may be desirable if the monitor does not comply with the BP22 standard or if the sensor equipment requires more power than a single channel of the monitor can provide. Circuitry 14 combines available monitor channels, each providing an excitation power signal, to achieve the total power and voltage required by the connected sensor equipment. Circuitry 14 (e.g., in the embodiment shown in FIG. 4) allows for accurate measurements of a physiological variable by flexible adaption of the reference voltage of a scaling circuit. Circuitry 14 may also enhance the accuracy of a sensor measurement by stabilizing the power supply to the connected sensor equipment and normalizing sensor sensitivity to the interface.

The construction and arrangement of the systems and methods as shown in the various exemplary embodiments are illustrative only. Although only a few embodiments have been described in detail in this disclosure, many modifications are possible (e.g., variations in structures of the various elements, values of parameters, mounting arrangements, use of materials, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A cable comprising:
   a first connector configured to receive power from a first channel of a physiological monitor and a second connector configured to receive power from a second channel of the monitor, wherein the power from each of the first and second channels of the monitor is combined within the cable;
   a third connector configured to provide the combined power to a receiver configured to receive information representing a measured physiological parameter and generate a signal representing the measured physiological parameter;
   a voltage converter configured to rescale the voltage of the combined power that is provided to the receiver;
   wherein the cable is configured to receive the signal representing the measured physiological parameter that is generated by the receiver, and
   wherein the cable is configured to provide a signal representing the measured physiological parameter to the monitor via the first connector and/or the second connector.

2. The cable of claim 1, wherein the first and second channels of the monitor do not comply with the BP22 standard governing excitation power signals.

3. The cable of claim 1, wherein the cable is configured to interface with a receiver requiring more power than the first channel of the monitor is configured to provide.

4. The cable of claim 1, wherein the measured physiological parameter is blood pressure.

5. The cable of claim 1, wherein the voltage converter is configured to double the voltage of the combined power.

6. The cable of claim 1, further comprising a plurality of filters configured to reduce noise.

7. The cable of claim 1, wherein the first connector and the second connector are disposed within a single housing configured to provide two connections to the monitor.

8. A method for connecting a receiver to a physiological monitor, comprising:
   using a cable, combining an excitation power signal received from a first channel of the monitor via a first connector of the cable and an excitation power signal received from a second channel of the monitor via a second connector of the cable, to form a combined power signal;
   using the cable, rescaling the voltage of the combined power signal;
   using the cable, providing the rescaled combined power signal to the receiver, via a third connector of the cable;
   using the receiver, wirelessly receiving information representing a measured physiological parameter, and generating a signal representing the measured physiological parameter;
   using the cable, receiving the signal representing the measured physiological parameter that is generated by the receiver,
   using the cable, providing the signal representing the measured physiological parameter to the monitor, via the first connector and/or the second connector of the cable.

9. The method of claim 8, wherein the first and second channels of the monitor do not comply with the BP22 standard governing excitation power signals.

10. The method of claim 8, wherein the receiver is a receiver requiring more power than the first channel of the monitor is configured to provide.

11. The method of claim 8, wherein the measured physiological parameter is blood pressure.

12. The method of claim 8, wherein the step of rescaling the voltage of the combined power signal includes doubling the voltage of the combined power signal.

13. The method of claim 8, further comprising filtering the combined power signal to reduce signal noise.

14. The method of claim 8, wherein the first connector and the second connector are disposed within a single housing configured to provide two connections to the monitor.

* * * * *